United States Patent
Madonia

(10) Patent No.: US 7,314,452 B2
(45) Date of Patent: Jan. 1, 2008

(54) SELF FLUSHING LUER ACTIVATED BLOOD SAMPLING DEVICES

(75) Inventor: James R. Madonia, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 11/360,311

(22) Filed: Feb. 23, 2006

(65) Prior Publication Data

US 2006/0155213 A1 Jul. 13, 2006

Related U.S. Application Data

(63) Continuation of application No. 11/329,406, filed on Jan. 10, 2006, now abandoned.

(60) Provisional application No. 60/643,053, filed on Jan. 10, 2005.

(51) Int. Cl.
*A61B 5/00* (2006.01)
*B65D 81/00* (2006.01)
*F15B 13/00* (2006.01)
*F16K 11/085* (2006.01)
*F16K 25/00* (2006.01)
*F16K 5/00* (2006.01)

(52) U.S. Cl. ............... 600/573; 137/271; 137/625.47; 251/181; 251/309

(58) Field of Classification Search ............. 600/573, 600/576, 579; 137/625.47, 625, 625.28; 251/366

See application file for complete search history.

(56) References Cited

U.S. PATENT DOCUMENTS

| | | | | |
|---|---|---|---|---|
| 3,557,778 A | * | 1/1971 | Hughes | 600/579 |
| 4,072,146 A | * | 2/1978 | Howes | 600/487 |
| 4,197,876 A | * | 4/1980 | Lobdell | 137/625.47 |
| 4,397,335 A | | 8/1983 | Doblar et al. | |
| 4,608,996 A | * | 9/1986 | Brown | 600/579 |
| 4,763,648 A | * | 8/1988 | Wyatt | 600/486 |
| 4,796,644 A | * | 1/1989 | Polaschegg | 600/573 |
| 4,981,140 A | * | 1/1991 | Wyatt | 600/486 |
| 5,002,066 A | * | 3/1991 | Simpson et al. | 600/573 |
| 5,074,334 A | | 12/1991 | Onodera | |
| 5,104,387 A | | 4/1992 | Pokorney et al. | |
| 5,148,811 A | * | 9/1992 | Messinger | 600/486 |
| 5,643,218 A | * | 7/1997 | Lynn et al. | 604/191 |
| 5,776,096 A | * | 7/1998 | Fields | 604/43 |
| 5,961,472 A | * | 10/1999 | Swendson et al. | 600/573 |
| 6,156,019 A | * | 12/2000 | Langevin | 604/323 |
| 6,269,704 B1 | | 8/2001 | Ziv et al. | |
| 6,626,884 B1 | * | 9/2003 | Dillon et al. | 604/409 |
| 6,918,893 B2 | * | 7/2005 | Houde et al. | 604/248 |
| 2001/0013370 A1 | | 8/2001 | Loo | |

* cited by examiner

*Primary Examiner*—Max Hindenburg
*Assistant Examiner*—Brian Szmal
(74) *Attorney, Agent, or Firm*—Gregory J. Carlin; Rajiv Yadav; David Hauser

(57) ABSTRACT

A blood sampling device for allowing a fluid pressure measurement and a fluid sample to be taken from a patient, having an inlet port configured to receive blood from the patient, an outlet port configured to be coupled to a monitoring channel having an infusion fluid, a sampling port configured for extraction of blood from the patient, a sampling channel configured to self-flush, after extraction, the blood with the infusion fluid, and an auxiliary channel for self-flushing the sampling channel.

7 Claims, 6 Drawing Sheets

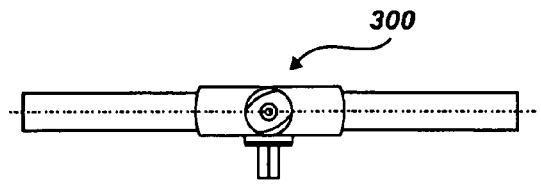
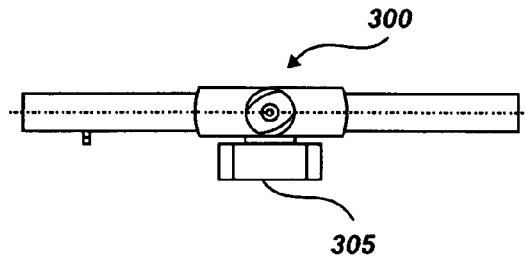
Fig. 3A
Fig. 3C
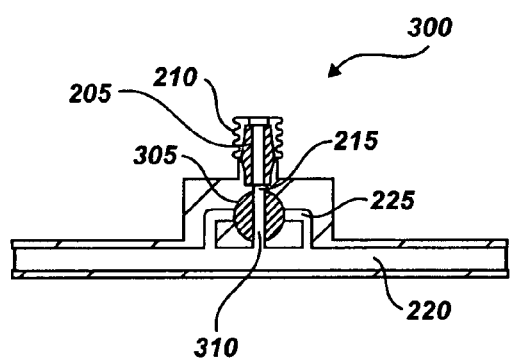
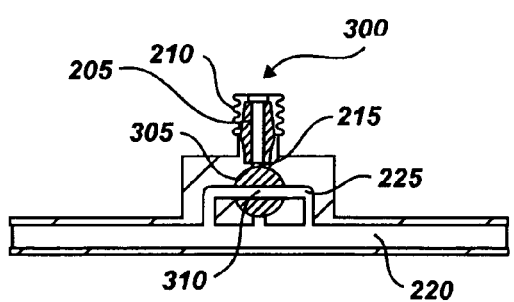
Fig. 3B
Fig. 3D

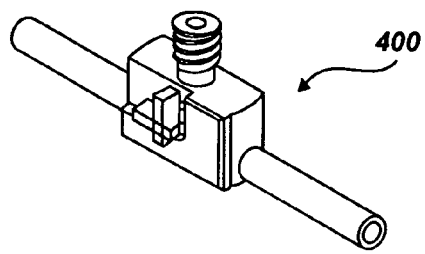
Fig. 4E
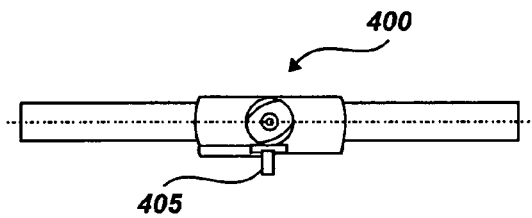 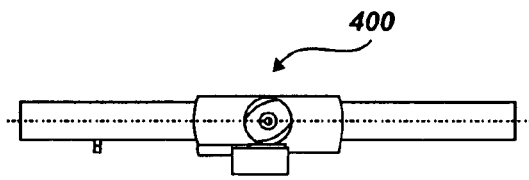
Fig. 4A  Fig. 4C
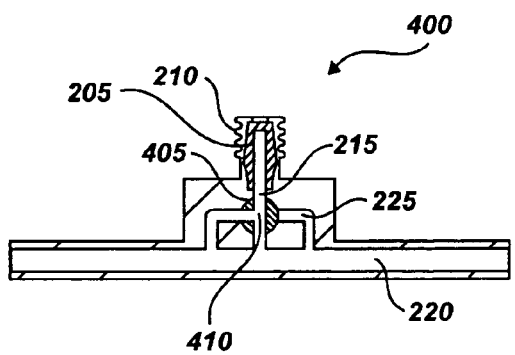 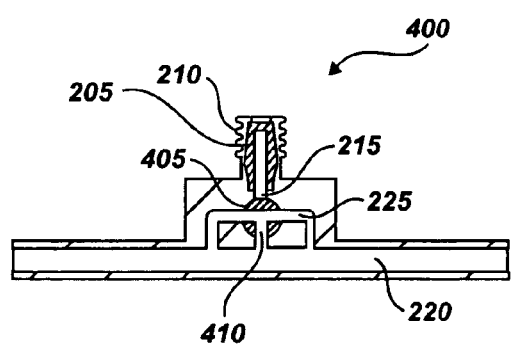
Fig. 4B  Fig. 4D

SELF FLUSHING LUER ACTIVATED BLOOD SAMPLING DEVICES

CROSS REFERENCE TO RELATED APPLICATIONS

This application is a continuation of and claims benefit of priority from U.S. patent application Ser. No. 11/329,406, filed Jan. 10, 2006, now abandoned which claims benefit of priority from U.S. Provisional Patent Application Ser. No. 60/643,053, filed Jan. 10, 2005, both of which are hereby incorporated by reference.

FIELD OF THE INVENTION

The invention relates generally to blood sampling devices, such as is commonly used at a blood sampling site, and more particularly to self flushing luer activated blood sampling devices.

DESCRIPTION OF THE RELATED ART

Blood sampling systems, such as Venous Arterial blood Management Protection (VAMP) systems, provide a safe and convenient method for withdrawing blood samples from a patient. Conventional VAMP systems typically consist of a fluid (e.g. pressure monitoring) line with a reservoir, a shutoff valve and a sampling site. The proximal end of the fluid line is coupled to an intravenous (IV) needle that is inserted into a patient's vein or artery. The distal end of the fluid line is coupled to pressure monitoring lines or continuous IV infusion or saline lines.

In the quiescent state, the shutoff valve is open allowing solution from the IV bag to be fed through the fluid line and the IV needle into the patient. To obtain a blood sample, the reservoir is slowly moved to an open position allowing the reservoir to fill with blood. The shutoff valve, located downstream from the reservoir, is then placed in a closed position preventing IV fluid from entering the blood sampling port. A needle of a syringe is inserted into the sampling port and blood is extracted therefrom. Some blood sampling systems utilize a luer configuration to couple the syringe or blood extractor to the sampling site. After the blood has been drawn, the needle is removed from the sampling site, the downstream shutoff valve is moved to the open position, and the reservoir is slowly returned to the closed position, thereby reestablishing the connection between the patient's circulatory system and the IV infusion or saline line.

While the VAMP system facilitates blood sampling without the need to puncture another needle or cannula into the patient, application of this technology has an undesirable consequence. For example, residual blood left in sampling sites can become a significant source of contamination and infection. Typically, the exterior surface of the sampling site is swabbed clean of any residual blood. However, the interior of the sampling sites cannot be swabbed clean. Furthermore, sampling sites with luer access, such as the CLAVE® Connector from ICU Medical Inc., do not have a flush exterior surface that can be swabbed clean. As a result, residual blood inside the luer can be a source of contamination and infection or can dry up and clog the luer access.

One approach to solve this problem is developing a self-flushing configuration that cleans the inside of the blood sampling system. Prior art blood sampling systems have used a Z-type configuration, where the inlet and outlet ports are positioned at different elevations. This configuration creates turbulence inside the blood sampling system, thereby resulting in the self-flushing of the blood inside the blood sampling system.

Although this Z-type configuration facilitates self-flushing, it degrades the quality of the pressure waveform when monitoring patient blood pressure. This is true because the Z-type configuration has a compliant member at the sampling site, such as a diaphragm, for needle or luer access, that is exposed to the fluid traveling through the blood sampling system. This exposed diaphragm distorts the signal when monitoring the patient's blood pressure.

With an increasing demand for improved blood sampling systems, there remains a continuing need in the art for a blood sampling system that self-flushes once the blood sampling procedure is completed while preventing the degradation of pressure waveform when monitoring the patient's blood pressure. It is to such improvements that the present invention is directed.

BRIEF DESCRIPTION OF THE DRAWINGS

Many of the advantages, object and features of the invention will become readily appreciated by reference to the following detailed description when considered in conjunction with the accompanying drawings in which like reference numerals description like parts throughout the figures, and wherein:

FIGS. 3A-D illustrate top and cross-sectional views of a blood sampling device with a ball valve in accordance with an embodiment of the present invention.

FIGS. 4A-E illustrate top, cross-sectional and perspective views of a blood sampling device with a ball cock in accordance with an embodiment of the present invention.

SUMMARY OF THE INVENTION

Figure 1:
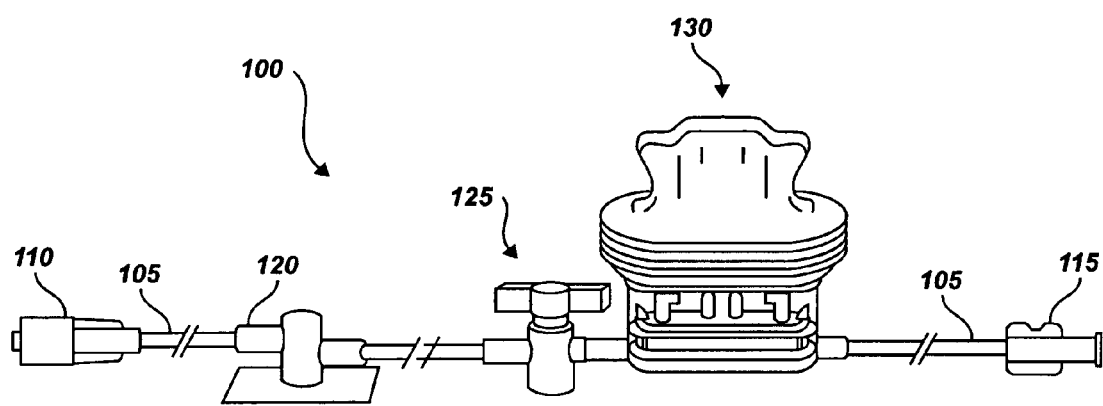
FIG. 1 is a perspective view of a prior art Venous Arterial blood Management Protection (VAMP) system.

A blood sampling device configured to self-flush once the blood sampling procedure is completed while preventing the degradation of pressure waveform when monitoring a patient's blood pressure. The blood sampling device allows fluid pressure measurement and blood sampling to be taken from the patient. The blood sampling device has an inlet port configured to receive blood from the patient, an outlet port configured to be coupled to a monitoring channel having an infusion fluid, a sampling port configured for extraction of blood from the patient, a sampling channel configured to self-flush, after extraction, the blood with the infusion fluid, and an auxiliary channel for self-flushing the sampling channel.

In one embodiment, the blood sampling device includes a rotatable paddle coupled to the sampling channel and orients the sampling channel to align with the auxiliary channel for self-flushing. In another embodiment, the blood sampling device has a ball valve configured to selectively allow the blood or the infusion fluid to flow through the sampling channel or the auxiliary channel. In one embodiment, the sampling port may be configured to allow a syringe to draw the blood while blocking access to the auxiliary channel. In another embodiment, the blood sampling device has a slide with an opening that selectively allows the flow of blood through the sampling channel or the flow of the infusion fluid through the auxiliary channel. In one embodiment, the blood sampling device has a stop cock that can selectively allow fluid to pass through at least one of the sampling channel, the auxiliary channel, or the monitoring channel. The stop cock may be configured to stop the flow of infusion fluid when the blood is being extracted.

The different embodiments of the blood sampling devices described herein advantageously do not require flushing with a physiological saline solution after a blood sample has been drawn. The blood sampling devices are "self flushing" after blood sampling, which provides a convenient benefit to the healthcare provider, and greater safety to the patient, by eliminating the potential for embolization of clotted blood if the sample site is not flushed properly.

DETAILED DESCRIPTION

Methods and systems that implement the embodiments of the various features of the invention will now be described with reference to the drawings. The drawings and the associated descriptions are provided to illustrate embodiments of the invention and not to limit the scope of the invention. Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment. Throughout the drawings, reference numbers are re-used to indicate correspondence between referenced elements. In addition, the first digit of each reference number indicates the figure in which the element first appears.

FIG. 1 is a perspective of a prior art Venous Arterial blood Management Protection (VAMP) system 100. The VAMP system 100 may include a fluid line 105 having a proximal end 110 and a distal end 115 relative to the patient. The VAMP system 100 may also include a blood sampling device 120, a valve 125 and a reservoir 130. The proximal end 110 of the fluid line 105 is coupled to an intravenous (IV) needle that is inserted into a patient's vein or artery. The distal end 115 of the fluid line 105 is coupled to pressure monitoring lines and/or continuous IV infusion (saline) line.

The blood sampling device 120 has a Z-type configuration with the inlet and outlet ports positioned at different elevations. This configuration creates turbulence inside the blood sampling device 120, thereby resulting in the self-flushing of the blood inside the blood sampling device 120.

The blood sampling device 120 has a compliant member at the sampling site, such as a diaphragm (not shown), for needle or luer access. To draw a sample of blood from the patient, the valve 125 is moved to a closed position, the reservoir 130 is moved to a closed position, and a syringe is positioned through the diaphragm of the blood sampling device 120 to draw blood from the patient. After the sample is drawn from the patient, the syringe is detached from the blood sampling device 120, the reservoir 130 is moved to an open position, and the valve 125 is moved to an open position. Since the diaphragm is exposed to the fluid traveling through the blood sampling device 120, it distorts the signal when monitoring the patient's blood pressure.

FIGS. 2A-D are top and cross-sectional views of a blood sampling device 200 in accordance with an embodiment of the present invention. The blood sampling device 200 may include a diaphragm 205 (e.g., a septum), a luer 210, a sampling channel 215, a monitoring or IV channel 220, an auxiliary channel 225, a passageway 235 and a paddle 230. The luer 210 can be configured to receive or attach to a cannula, which is attached to a syringe (not shown in the Figure). The sampling channel 215 can be used for blood sampling, and the monitoring channel 220 can be used for monitoring the patient's blood pressure. The auxiliary channel 225 allows the blood sampling device 200 to "self flush" after blood sampling is completed. In one embodiment the monitoring channel 220 can have a diameter of approximately 0.2 inches, while the auxiliary channel 225 can have a diameter of approximately 0.05 inches. At a proximal end or portion, the monitoring channel 220 can include an inlet port for receiving blood. At a distal end or portion the monitoring channel 220 can include an outlet port end for receiving a flushing fluid, such as saline.

The paddle 230 can be hinged to the blood sampling device 200 to allow for rotational movement about a central axis. The paddle is coupled to the passageway 235, such that when the paddle 230 is rotated, the passageway 235 rotates the axis as well. The passageway 235 provides a path for blood to flow from the patient's circulatory system through the sampling channel 215 and into the syringe.

Figure 2A:
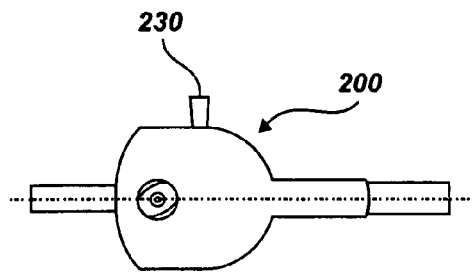
FIGS. 2A-D illustrate top and cross-sectional views of a blood sampling device with a paddle in accordance with an embodiment of the present invention.
Figure 2C:
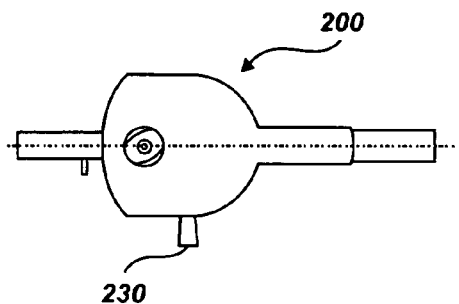
Figure 2B:
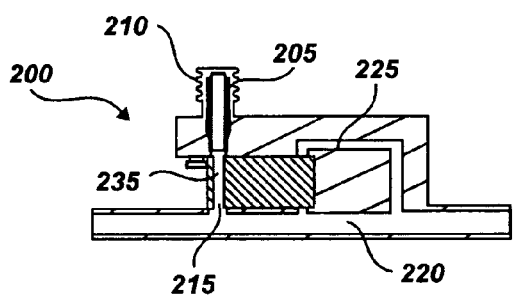
Figure 2D:
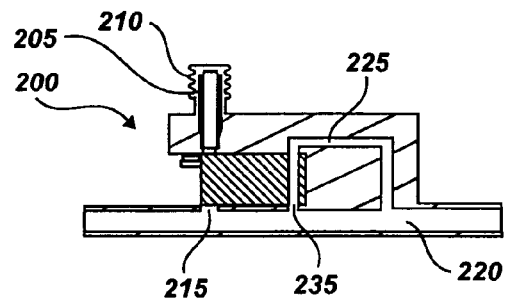

The blood sampling device 200 can operate in a blood sampling mode (FIGS. 2A and B) and a pressure monitoring mode (FIGS. 2C and D). To draw a sample of blood from the patient, the valve 125 (shown in FIG. 1) is closed to stop the flow of IV infusion fluid to the patient. Next, the paddle 230 is rotated to a first position, shown in FIG. 2A, that allows blood to flow through the sampling channel 215, the passageway 235 and into the syringe. After the sample is drawn from the patient, the valve 125 is opened and the paddle 230 can be rotated to a second position, shown in FIG. 2C, that allows the IV infusion fluid to flow through the auxiliary channel 225 and the passageway 235. This rotational movement isolates the diaphragm 205 from the IV infusion fluid traveling through the blood sampling device 200. Hence, this embodiment provides a "self-flushing" mechanism that clears blood residue after blood sampling and isolates the diaphragm 205 during pressure monitoring.

FIGS. 3A-D are top and cross-sectional views of a blood sampling device 300 in accordance with an embodiment of the invention. The blood sampling device 300 may include the diaphragm 205, the luer 210, the sampling channel 215, the monitoring channel 220, the auxiliary channel 225 and a ball valve 305. The ball valve 305 has a passageway 310 to allow fluid to pass therethrough.

The blood sampling device 300 can operate in a blood sampling mode (FIGS. 3A and B) and a pressure monitoring mode (FIGS. 3C and D). To draw a sample of blood from the patient, the valve 125 (shown in FIG. 1) is closed to stop the flow of IV infusion fluid to the patient. Once a sample is drawn from the patient, the valve 125 is opened to allow the flow of IV infusion fluid to the patient. In the blood sampling mode, the ball valve 305 is rotated to a first position that allows blood to flow through the sampling channel 215, the passageway 310 and into the syringe. In the pressure monitoring mode, the ball valve 305 is rotated to a second position that blocks the flow of fluid through the sampling channel 215 and allows the flow of IV infusion fluid through the auxiliary channel 225 and the passageway 310. This rotational movement isolates the diaphragm 205 from the IV infusion fluid traveling through the blood sampling device 300. Hence, this embodiment provides a "self-flushing" mechanism that clears blood residue after blood sampling and isolates the diaphragm 205 during pressure monitoring.

FIGS. 4A-E are top, cross-sectional, and perspective views of a blood sampling device 400 in accordance with an embodiment of the invention. The blood sampling device 400 may include the diaphragm 205, the luer 210, the sampling channel 215, the monitoring channel 220, the auxiliary channel 225 and a stop cock 405. The stop cock 405 has a T-shaped passageway 410 that can selectively allow fluid to pass therethrough to the sampling channel 215, the auxiliary channel 225, or the monitoring channel 220.

The blood sampling device 400 can operate in a blood sampling mode (FIGS. 4A and B) and a pressure monitoring mode (FIGS. 4C and D). To draw a sample of blood from the patient, the valve 125 (shown in FIG. 1) is closed to stop the flow of IV infusion fluid to the patient. Once a sample is drawn from the patient, the valve 125 is opened to allow the flow of IV infusion fluid to the patient. In the blood sampling mode, the stop cock 405 is positioned to selectively allow blood flow through the passageway 410, the sampling channel 215 and a segment of the auxiliary channel 225. In the pressure monitoring mode, the stop cock 405 is positioned to block the flow of fluid through the sampling channel 215, while selectively allowing the flow of the fluid through the sampling channel 215, the auxiliary channel 225, and the monitoring channel 220. This selective positioning of the stop cock 405 isolates the diaphragm 205 from the IV infusion fluid traveling through the blood sampling device 400. Hence, this embodiment provides a "self-flushing" mechanism that clears blood residue after blood sampling and isolates the diaphragm 205 during pressure monitoring.

FIGS. 5A-D are top and cross-sectional views of a blood sampling device 500 in accordance with an embodiment of the invention. The blood sampling device 500 may include the diaphragm 205, the luer 210, the sampling channel 215, the monitoring channel 220, the auxiliary channel 225 and a slide 505. The slide 505 has a passageway 510 to allow fluid to pass therethrough.

Figure 5A:
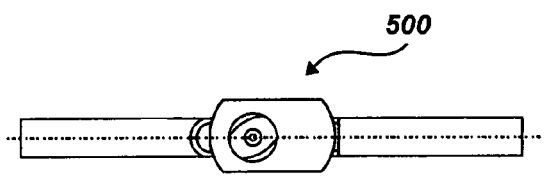
FIGS. 5A-D illustrate top and cross-sectional views of a blood sampling device with a slide in accordance with an embodiment of the present invention.
Figure 5C:
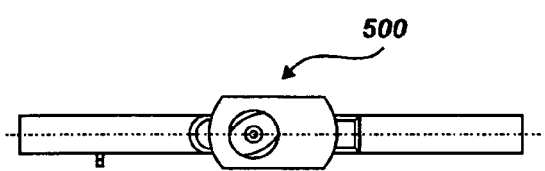
Figure 5B:
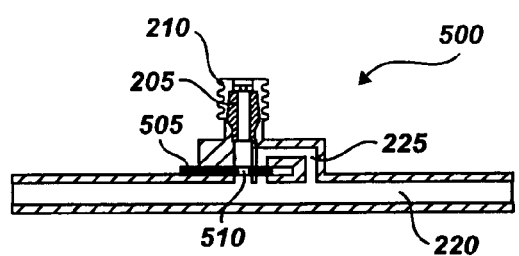
Figure 5D:
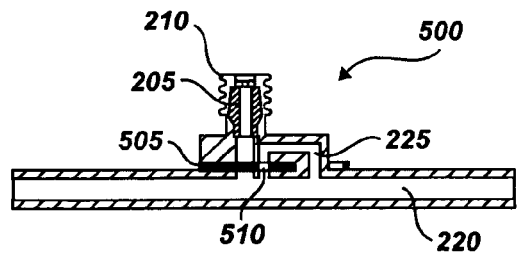

The blood sampling device 500 can operate in a blood sampling mode (FIGS. 5A and B) and a pressure monitoring mode (FIGS. 5C and D). To draw a sample of blood from the patient, the valve 125 (shown in FIG. 1) is closed to stop the flow of IV infusion fluid to the patient. Once a sample is drawn from the patient, the valve 125 is opened to allow the flow of IV infusion fluid to the patient. In the blood sampling mode (FIGS. 5A and B), the slide 505 is positioned to selectively allow blood flow through the passageway 510 and the sampling channel 215, while closing one end of the auxiliary channel 225. In the pressure monitoring mode (FIGS. 5C and D), the slide 505 is positioned to block the flow of fluid through the sampling channel 215 and allows the flow of the IV infusion fluid through the auxiliary channel 225 and the passageway 510. This isolates the diaphragm 205 from the IV infusion fluid traveling through the blood sampling device 500. Hence, this embodiment provides a "self-flushing" mechanism that clears blood residue after blood sampling and isolates the diaphragm 205 during pressure monitoring.

The different embodiments of the blood sampling devices described herein advantageously do not require flushing with a physiological saline solution after a blood sample has been drawn. The blood sampling devices are "self flushing" after blood sampling, which provides a convenient benefit to the healthcare provider, and greater safety to the patient, by eliminating the potential for embolization of clotted blood if the sample site is not flushed properly. In one embodiment, the blood sampling devices may eliminate the need for the valve 125. In another embodiment, the fidelity of the pressure wave form can be enhanced by isolating the sampling channel 215 septum from the monitoring channel 220.

FIGS. 6A-E are top, cross-sectional, and perspective views of a blood sampling device 600 in accordance with an embodiment of the invention. The blood sampling device 600 may include the diaphragm 205, the luer 210, the sampling channel 215, the monitoring channel 220, the auxiliary channel 225 and a stop cock 605. The stop cock 605 has a T-shaped passageway 610 that can selectively allow fluid to pass therethrough to the sampling channel 215, the auxiliary channel 225, or the monitoring channel 220. The stop cock 605 is coupled to the monitoring channel 220 to control the flow of the IV infusion fluid through the monitoring channel 220, while allowing for the self-flushing capability after blood sampling. This configuration eliminates the need to use a valve 125 upstream at the distal end 115 of the fluid line 105.

Figure 6E:
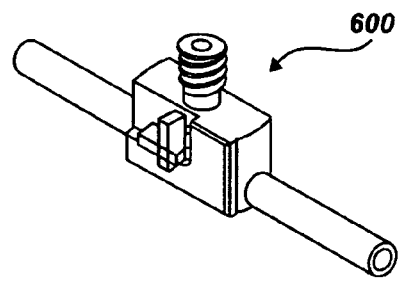
FIGS. 6A-E illustrate top, cross-sectional, and perspective views of a blood sampling device with a ball cock positioned in the monitoring channel, in accordance with an embodiment of the present invention.
Figures 6A, 6C:
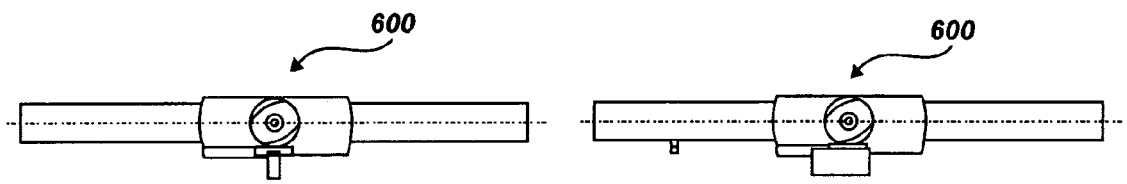
Figures 6B, 6D:
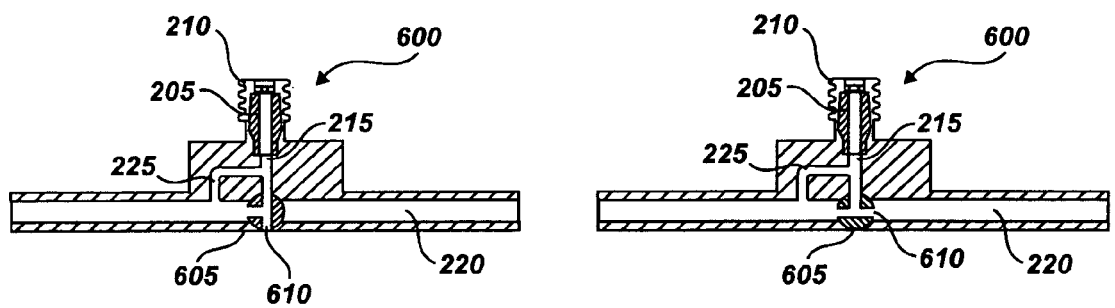

The blood sampling device 600 can operate in a blood sampling mode (FIGS. 6A and B) and a pressure monitoring mode (FIGS. 6C and D). To draw a sample of blood from the patient, the stop cock 605 is rotated to a position that stops the flow of IV infusion fluid to the patient. Once a sample is drawn from the patient, the stop cock 605 is rotated back to allow the flow of IV infusion fluid to the patient while self-flushing the passageway 610, the sampling channel 215, and the auxiliary channel 225.

In the blood sampling mode, the stop cock 605 is positioned to selectively allow blood flow through the passageway 610, the sampling channel 215 and a segment of the auxiliary channel 225. In the pressure monitoring mode, the stop cock 605 is positioned to allow the flow of fluid through the sampling channel 215, the auxiliary channel 225, and the monitoring channel 220. This configuration, however, allows the diaphragm 205 to be exposed to the fluid traveling through the auxiliary channel 225. Hence, this embodiment provides a "self-flushing" mechanism that clears blood residue after blood sampling, eliminates the need for a valve 125 upstream in the monitoring channel 220 to stop the flow of IV infusion fluid, but does not isolate the diaphragm 205 from the IV infusion fluid.

What is claimed is:

1. An apparatus for allowing a fluid pressure measurement and a fluid sample to be taken from a patient, comprising:
   an inlet port configured to receive a first fluid from the patient;
   an outlet port coupled to the inlet port through a monitoring channel and configured to receive a second fluid;
   a sampling port configured for extraction of the first fluid from the patient;
   an auxiliary channel having first and second ends, the first end coupled to the outlet port; and
   a four-port two-position sampling valve having a passageway, the sampling valve in a first position connecting the sampling port to the inlet port and the sampling valve in a second position connecting the second end of the auxiliary channel to the passageway for self-flushing the passageway with the second fluid.

2. The apparatus of claim 1, wherein the sampling port is configured to receive a syringe.

3. The apparatus of claim 1, wherein the sampling port is configured to receive a cannula.

4. A blood sampling device, comprising:
- an outlet port configured receive blood from a patient;
- an outlet port coupled to the inlet port through a monitoring channel and configured to receive an infusion fluid;
- a sampling port configured for extraction of blood from the patient;
- an auxiliary channel between the inlet port and the sampling port; and
- a device having a passageway movable between first and second positions, the device in the first position isolating the inlet port from the outlet port and coupling the inlet port to the sampling port and the device in the second position forming two flow paths for the infusion fluid from the outlet port to the inlet port, including a flow path through the auxiliary channel for flushing blood from the passageway.

5. The blood sampling device of claim 4 wherein the device is a ball valve.

6. The blood sampling device of claim 4 wherein the sampling port is configured to allow a needle to draw the blood while blocking access to the auxiliary channel.

7. The blood sampling device of claim 5 wherein the passageway forms a T-shaped intersection within the ball valve.

* * * * *